(12) United States Patent
Lichtenberg et al.

(10) Patent No.: US 6,939,840 B2
(45) Date of Patent: Sep. 6, 2005

(54) DISINFECTANT

(75) Inventors: Florian Lichtenberg, Grenzach-Wyhlen (DE); Michael Lützeler, Grenzach-Wyhlen (DE); Volker Ranft, Murg (DE)

(73) Assignee: Lonza AG, Basel (CH)

( * ) Notice: Subject to any disclaimer, the term of this patent is extended or adjusted under 35 U.S.C. 154(b) by 171 days.

(21) Appl. No.: 10/381,010
(22) PCT Filed: Sep. 18, 2001
(86) PCT No.: PCT/EP01/10754
§ 371 (c)(1),
(2), (4) Date: Mar. 20, 2003
(87) PCT Pub. No.: WO02/23990
PCT Pub. Date: Mar. 28, 2002

(65) Prior Publication Data
US 2004/0029767 A1 Feb. 12, 2004

(30) Foreign Application Priority Data
Sep. 20, 2000 (EP) .......................... 00120590

(51) Int. Cl.⁷ .............................. C11D 1/62; C11D 3/26; C11D 3/30; C11D 3/43
(52) U.S. Cl. ................... 510/384; 510/382; 510/499; 510/504; 510/123; 510/130
(58) Field of Search .................. 510/382, 384, 510/499, 504, 123, 130, 191, 319; 422/28

(56) References Cited

U.S. PATENT DOCUMENTS

| 4,454,983 A | 6/1984 | Tarvis, Jr. |
| 5,908,854 A | 6/1999 | McCue et al. |

FOREIGN PATENT DOCUMENTS

| EP | 0333143 | 3/1998 |
| EP | 1025967 | 8/2000 |
| FR | 2602955 | 8/1986 |
| JP | 5-85905 | 4/1993 |
| JP | 50-132126 | 10/1995 |
| JP | 10-87410 | 10/1998 |
| WO | 93-15173 | 8/1993 |
| WO | WO98/17763 | * 4/1998 |
| WO | 98-20732 | 5/1998 |
| WO | 99-15012 | 9/1998 |

OTHER PUBLICATIONS

International Search Report from corresponding International Patent application.
Database WPI, Section Ch, Week 199946, Derwent Publications Ltd., An 1999–541231, XP002190404, Jul. 1999.
Database WPI, Section Ch, Week 199824, Derwent Publications Ltd., AN 1998–266961, XP002190405, Apr. 1998.
Database CA 'Online', Chemical Abstracts Service, Columbus, OH, US, Accession No. 134:168324 CA, ZP002190403, Jul. 2000.
Database WPI, Section Ch, Week 197749, Derwent Publications Ltd., AN 1977–87079Y, XP002190406, Oct. 1975.
Database CA 'Online', Chemical Abstracts Service, Columbus, OH, US, Accession No. 105:99132 CA, XP002190402, Dec. 1985.
Database WPI, Section Ch, Week 199318, Derwent Publications Ltd., AN 1993–149118, XP002190407, Apr. 1998.

* cited by examiner

Primary Examiner—Gregory R. Del Cotto
(74) Attorney, Agent, or Firm—Fisher Christen & Sabol

(57) ABSTRACT

Disinfectant compositions, containing (a) at least one amine and/or quaternary ammonium salt of the general formula (Ia) or (Ib):

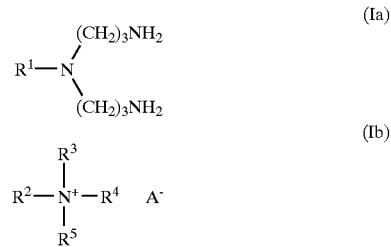

wherein $R^1$ represents $C_{6-18}$ alkyl, $R^2$ represents benzyl or $C_{6-18}$ alkyl, $R^3$ represents $C_{1-18}$ alkyl or $-[CH_2)_2-O]_nR^6$, where n=1–20, $R^4$ and $R^5$ independently of one another represent $C_{1-4}$ alkyl, $R^6$ represents hydrogen or optionally substituted phenyl and $A^-$ is a monovalent anion or the equivalent of a multivalent anion of an inorganic or organic acid; and (b) at least one alkanolamine of the general formula (II):

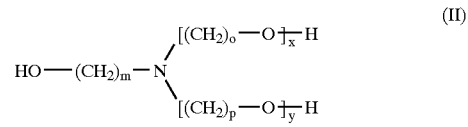

wherein m and, if present, o and p independently of one another have the values 2 or 3 and x and y independently of one another have the values 0 or 1, or a corresponding salt. The mass ratio of the components in the formulas (I):(II) is between 20:1 and 1:20. The compositions are characterized by an excellent bactericidal and in particular fungicidal action even in small application concentrations and are suitable for use as both disinfectants and preservative agents.

10 Claims, No Drawings

DISINFECTANT

This is a 371 U.S. national stage application of International Patent Application PCT/EP01/10754, filed on Sep. 18, 2001, that has priority benefit of European Patent Application No. 00120590.5, filed on Sep. 20, 2000.

The invention relates to synergistic disinfectant compositions based on amines and/or quaternary ammonium salts.

Numerous disinfectant and preservative compositions based on mines and/or quaternary ammonium salts are known. However, in general, in particular at relatively high dilution, these exhibit an unsatisfactory activity towards fungi, for example *Aspergillus niger*.

It was therefore an object of the present invention to provide disinfectant compositions, based on amines and/or quaternary ammonium salts which exhibit good activity towards fungi even at high dilution.

This object is achieved according to the invention by the disinfectant composition of the invention.

It has surprisingly been found that amines and/or quaternary ammonium salts of the general formula

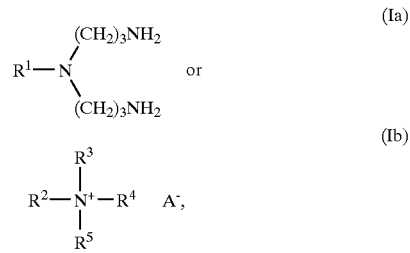

where $R^1$ is $C_{6-18}$-alkyl
$R^2$ is benzyl or $C_{6-18}$-alkyl
$R^3$ is $C_{1-18}$-alkyl or $-[(CH_2)_2-O]_nR^6$ where n=1–20
$R^4$ and $R^5$ independently of one another are $C_{1-4}$-alkyl
$R^6$ is hydrogen or unsubstituted or substituted phenyl and
$A^-$ is a monovalent anion or one equivalent of a polyvalent anion of an inorganic or organic acid;
by addition of at least one alkanolamine of the general formula

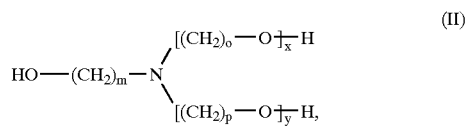

where m and, if present, o and p independently of one another have the value 2 or 3 and x and y independently of one another have the value 0 or 1, or a corresponding salt; in the mass ratio (I):(II) of 20:1 to 1:20 obtain good fungicidal activity.

Alkyl, here and hereinafter, is taken to mean in each case unbranched or branched alkyl groups of the specified number of carbons, but preferably unbranched alkyl groups, and particularly preferably those having an even number of carbon atoms. In particular, this is also taken to mean the homologue mixtures derived from natural raw materials, for example "coconutalkyl".

Substituted phenyl is taken to mean, in particular, phenyl groups substituted with one or more $C_{1-8}$-alkyl groups and/or chlorine atoms.

Suitable anions $A^-$ are in principle all inorganic or organic anions, in particular halide, for example chloride or bromide, or anions of low carboxylic acids, for example acetate, propionate or lactate.

The amine or quaternary ammonium salt (Ia/Ib) is preferably N,N-bis(3-aminopropyl)dodecylamine, N,N-bis(3-aminopropyl)octylamine, a didecyldimethylammonium salt, dioctyldimethylammonium salt, octyldecyldimethylammonium salt, dicoconutalkyldimethylammonium salt, coconutalkyldimethylpoly(oxyethyl)ammonium salt, dicoconutalkylmethylpoly(oxyethyl)ammonium salt, decyldimethylpoly(oxyethyl) ammonium salt, didecylmethylpoly(oxyethyl)ammonium salt, octyldimethylpoly(oxyethyl)ammonium salt, dioctylmethylpoly(oxyethyl)ammonium salt, coconutalkyldimethylbenzylammonium salt, benzyldodecyldimethylammonium salt or benzyldimethylpoly(oxyethyl) ammonium salt or a mixture of two or more of these compounds.

Suitable alkanolamines (II) are in principle all ethanolamines and propanolamines, in particular monoethanolamine, diethanolamine, triethanolamine and 3-amino-1-propanol. Obviously, using mixtures of the said compounds is also within the scope of the invention. Particularly good results have been obtained using the compounds having a primary amino group, that is to say using monoethanolamine and 3-amino-1-propanol.

The mass ratio of amine (Ia) or quaternary ammonium salt (Ib) to alkanolamine (II) is preferably in the range from 1:5 to 5:1.

The inventive disinfectant compositions preferably comprise water as solvent, if appropriate in combination with an organic solvent.

Preferably, the inventive disinfectant compositions further comprise one or more aids selected from the group consisting of organic solvents, surfactants, complexing agents, fragrances and colorants.

A preferred field of application of the inventive disinfectant compositions is surface disinfection and instrument disinfection, Further preferred fields of application are laundry disinfection and hand disinfection.

The inventive disinfectant compositions are also suitable for use in chemical toilets, for example on board aircraft and vehicles.

A further preferred field of use is the preservation of industrial liquids, for example water circulation in paper manufacturing, cooling water, belt lubricants for conveyor belts, or cutting fluids in metal machining.

An application which is likewise preferred is finally the use as preservative for construction materials which are organic or susceptible to biological attack, for example wood.

The examples below illustrate the implementation of the invention, and should not be taken to be a restriction to the embodiments described. All quantities given, where not otherwise specified, are in % by mass. The test microorganism used in each case was *Aspergillus niger* ATCC 16404. The effectiveness was determined, unless otherwise specified, using the method specified in CEN 1275.

EXAMPLE 1

A disinfecting cleaner formulation (concentrate) was prepared from:

5.0% didecyldimethylammonium chloride (50% strength solution)
2.0% N,N-bis(3-aminopropyl)dodecylamine
5.0% monoethanolamine
5.0% Genapol® T250 (tallow fatty alcohol polyglycol ether, 25 mol of ethylene oxide)

0.5% sodium metasilicate
0.5% sodium carbonate
2.0% methylglycinediacetic acid trisodium salt (Trilon® M; 40% strength solution) water to 100%

The effectiveness was determined using a dilution (1 part of concentrate, 99 parts of wat r) at 20° C. and with a contact time of 15 min. The logarithm to base ten of the reduction in microorganism count was 4.1.

Comparative Example 1

The procedure of Example 1 was followed, but with the difference that the monoethanolamine was replaced by the same amount of water. Under the same test conditions, the formulation was virtually inactive.

EXAMPLE 2

A disinfectant formulation (concentrate) was prepared from:
4.9% N,N-bis(3-aminopropyl)dodecylamine
4.0% monoethanolamine
2.0% Genapol® T250 (tallow fatty alcohol polyglycol ether, 25 mol of ethylene oxide)
5.0% Hostapur® SAS 30 ($C_{13-17}$ secondary n-alkanesulphonic acid, sodium salt)
2.0% ethylenediaminetetraacetic acid tetrasodium salt (40% strength solution)
0.7% ethylenediaminetetraacetic acid water to 100%

The effectiveness was determined using a dilution (1 part of concentrate, 199 parts of water) at 20° C. and with a contact time of 15 min. The logarithm to base ten of the reduction in microorganism count was 4.3.

EXAMPLE 3

A disinfectant formulation (concentrate) was prepared from:
4.2% N,N-bis(3-aminopropyl)dodecylamine
2.0% didecylmethylpoly(oxyethyl)ammonium propionate (BARDAP 26)
4.0% monoethanolamine
2.0% Genapol® T250 (tallow fatty alcohol polyglycol ether, 25 mol of ethylene oxide)
5.0% Hostapur® SAS 30 ($C_{13-17}$ secondary n-alkanesulphonic acid, sodium salt)
2.0% ethylenediaminetetraacetic acid tetrasodium salt (40% strength solution)
0.7% ethylenediaminetetraacetic acid
4.0% butyl diglycol water to 100%

The effectiveness was determined using a dilution (1 part of concentrate, 199 parts of water) at 20° C. and with a contact time of 15 min. The logarithm to base ten of the reduction in microorganism count was >4.4. In addition, the effectiveness was also determined using the method specified in CEN 1650 with a contact time of 15 min, a concentration of 1.0%, a water hardness of 30° fH and an organic load of 0.3% albumin. The logarithm of the reduction in microorganism count was >4.4.

EXAMPLES 4–19

Aqueous solutions were prepared from 0.5% alkanolamine (II) and 0.25% of amine or quaternary ammonium salt (Ia/Ib) and tested using the method specified in CEN 1275. The results are summarized in Table 1.

TABLE I

| Example No. | Amine/ammonium salt | Alkanolamine | log microbial reduction |
|---|---|---|---|
| 4 | dimethyldioctyl-ammonium chloride | monoethanolamine | 4.3 |
| 5 | ditto | diethanolamine | 4.0 |
| 6 | ditto | triethanolamine | 3.6 |
| 7 | ditto | 3-amino-1-propanol | 4.2 |
| 8 | didecyldimethyl-ammonium chloride | monoethanolamine | 4.0 |
| 9 | ditto | diethanolamine | 3.8 |
| 10 | ditto | triethanolamine | 3.1 |
| 11 | ditto | 3-amino-1-propanol | 4.0 |
| 12 | di-$C_{8-10}$-alkyldimethyl-ammonium chloride (60%)/$C_{12-16}$-alkyl-benzyldimethylammonium chloride (40%); Bardac® 205-M | monoethanolamine | 3.9 |
| 13 | ditto | diethanolamine | 3.2 |
| 14 | ditto | triethanolamine | 2.8 |
| 15 | ditto | 3-amino-1-propanol | 3.8 |
| 16 | N,N-bis(3-aminopropyl)dodecylamine | monoethanolamine | 2.9 |
| 17 | ditto | diethanolamine | 2.7 |
| 18 | ditto | triethanolamine | 2.4 |
| 19 | ditto | 3-amino-1-propanol | 2.8 |

For comparison, all compounds listed in Table 1 were tested as individual substances in 0.5% strength solution. None of these compounds exhibited pronounced fungicidal activity (log microbial reduction <2).

What is claimed is:
1. A disinfectant composition comprising:

i) an amine and, optionally a quaternary ammonium salt, the amine (Ia) has formula:

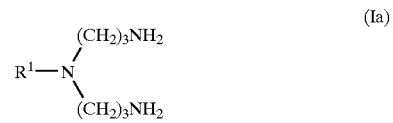

(Ia)

where $R^1$ is $C_{6-18}$-alkyl; and the quaternary ammonium salt has the formula:

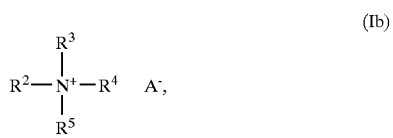

(Ib)

where $R^2$ is benzyl or $C_{6-18}$-alkyl;
$R^3$ is $C_{1-18}$-alkyl or —[$(CH_2)_2$—O]$_n$$R^6$ where n=1–20;
$R^4$ and $R^5$ independently of one another are $C_{1-4}$-alkyl;
$R^6$ is hydrogen or unsubstituted or substituted phenyl; and A⁻ is a monovalent anion or one equivalent of a polyvalent anion of an inorganic or organic acid, and
(ii) at least one alkanolamine of the formula;

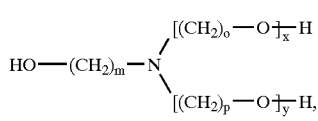

where m and, if present, o and p independently of one another have the value 2 or 3; and
x and y independently of one another have the value 0 or 1, or a corresponding salt;
in the mass ratio (I):(II): of 20:1 to 1:20.

2. The disinfectant composition according to claim 1, wherein the amine or quaternary ammonium salt is selected from the group consisting of N,N-bis(3-aminopropyl) dodecylamine, N,N-bis(3-aminopropyl)octylamine, didecyldimethylammonium salts, dioctyldimethylammonium salts, octyldecyldimethylammonium salts, coconutalkyldimethylbenzylammonium salts and benzyldimethyloxoethylammonium salts and mixtures of these compounds.

3. The disinfectant composition according to claim 1, wherein the alkanolamine (II) is selected from the group consisting of monoethanolamine, diethanolamine, triethanolamine and 3-amino-1-propanol.

4. The disinfectant composition according to claim 1, wherein the mass ratio (I):(II) is between 1:5 and 5:1.

5. The disinfectant composition according to claim 1, wherein the disinfectant composition includes water as a solvent.

6. The disinfectant composition according to claim 1, wherein the disinfectant composition additionally comprises one or more aids selected from the group consisting of organic solvents, surfactants, complexing agents, fragrances and colorants.

7. The disinfectant composition according to claim 2, wherein the alkanolamine (II) is selected from the group consisting of monoethanolamine, diethanolamine, triethanolamine and 3-amino-1-propanol.

8. The disinfectant composition according to claim 3, wherein the mass ratio (I):(II) is between 1:5 and 5:1.

9. The disinfectant composition according to claim 4, wherein the disinfectant composition includes water as solvent.

10. The disinfectant composition according to claim 5, wherein the disinfectant composition additionally comprises one or more aids selected from the group consisting of organic solvents, surfactants, complexing agents, fragrances and colorants.

* * * * *